United States Patent
Doan et al.

(12) 
(10) Patent No.: US 6,198,973 B1
(45) Date of Patent: Mar. 6, 2001

(54) INTEGRATED STEROID ELUTING PACING TIP ELECTRODE

(75) Inventors: Phong Doan, Stevenson Ranch; Lisa Caffee, Cayon County; Yougandh Chitre, Stevenson Ranch, all of CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 09/320,405

(22) Filed: May 26, 1999

(51) Int. Cl.$^7$ .................................................. A61N 1/04
(52) U.S. Cl. .................................................... 607/120
(58) Field of Search ............................ 607/120, 122, 607/119, 121

(56) References Cited

U.S. PATENT DOCUMENTS

| | | | |
|---|---|---|---|
| 4,236,529 | 12/1980 | Little | 128/785 |
| 4,408,604 | 10/1983 | Hirshorn et al. | 128/785 |
| 4,440,178 | 4/1984 | Bussard et al. | 128/784 |
| 4,485,813 | 12/1984 | Anderson et al. | 128/675 |
| 4,506,680 | 3/1985 | Stokes | 128/786 |
| 4,577,642 | 3/1986 | Stokes | 128/784 |
| 4,606,118 | 8/1986 | Cannon et al. | 29/825 |
| 4,690,155 | 9/1987 | Hess | 128/786 |
| 4,819,661 | 4/1989 | Heil, Jr. et al. | 128/786 |
| 4,819,662 | 4/1989 | Heil, Jr. et al. | 128/786 |
| 4,844,099 | 7/1989 | Skalsky et al. | 128/785 |
| 4,848,352 | 7/1989 | Pohndorf et al. | 128/642 |
| 4,953,564 | 9/1990 | Berthelsen | 128/784 |
| 5,002,067 | 3/1991 | Berthelsen et al. | 128/786 |
| 5,003,992 | 4/1991 | Holleman et a l. | 128/785 |
| 5,324,325 | 6/1994 | Moaddeb | 607/120 |
| 5,433,742 | 7/1995 | Willis | 607/122 |
| 5,438,987 | 8/1995 | Thacker et al. | 128/634 |
| 5,447,533 | 9/1995 | Vachon et al. | 607/120 |
| 5,496,360 | 3/1996 | Hoffmann et al. | 607/120 |
| 5,531,780 | 7/1996 | Vachon | 607/120 |
| 5,531,781 | 7/1996 | Alferness et al. | 607/122 |
| 5,545,161 | 8/1996 | Imran | 606/41 |
| 5,571,162 | 11/1996 | Lin | 607/122 |
| 5,575,814 | 11/1996 | Giele et al. | 607/127 |
| 5,582,609 | 12/1996 | Swanson et al. | 606/39 |
| 5,755,762 | 5/1998 | Bush | 607/122 |
| 5,755,763 | 5/1998 | Farfel | 607/122 |
| 5,833,715 | 11/1998 | Vachon et al. | 607/120 |
| B1 4,711,251 | 6/1994 | Stokes | 607/116 |

Primary Examiner—Scott M. Getzow

(57) ABSTRACT

An electrode assembly for a body implantable lead comprises a longitudinally extending dispenser housing having an internal cavity with opposed longitudinally extending openings for storing a drug to be dispensed. A tip electrode integral and axially aligned with the dispenser housing has a face adapted for positioning adjacent the desired body site, a transverse channel formed into and transversely across its face, and an orifice extending between the channel and the internal cavity for elution of the drug to the desired body site. A weld sleeve integral and axially aligned with the dispenser housing distant from the tip electrode has an outer peripheral surface for engageably receiving one end of an elongated electrical conductor, and a collar spaced from the dispenser housing. The electrical conductor is welded to the collar to obtain a welded connection for electrical continuity between the tip electrode and the electrical conductor. An insulative sheath of resilient material is fittingly received on the outer peripheral surface of the dispenser housing overlying the longitudinally extending openings and the welded connection between the electrical conductor and the weld sleeve. Insulative tubing is received on the coiled conductor includes a skirt member distant from the tip electrode and coaxial with the insulative tubing and biased radially into engagement with the outer peripheral surface of the insulative tubing. A plurality of fixation tines are integral with, and extend radially outwardly from, the insulative sheath at a plurality of circumferentially spaced locations.

12 Claims, 3 Drawing Sheets

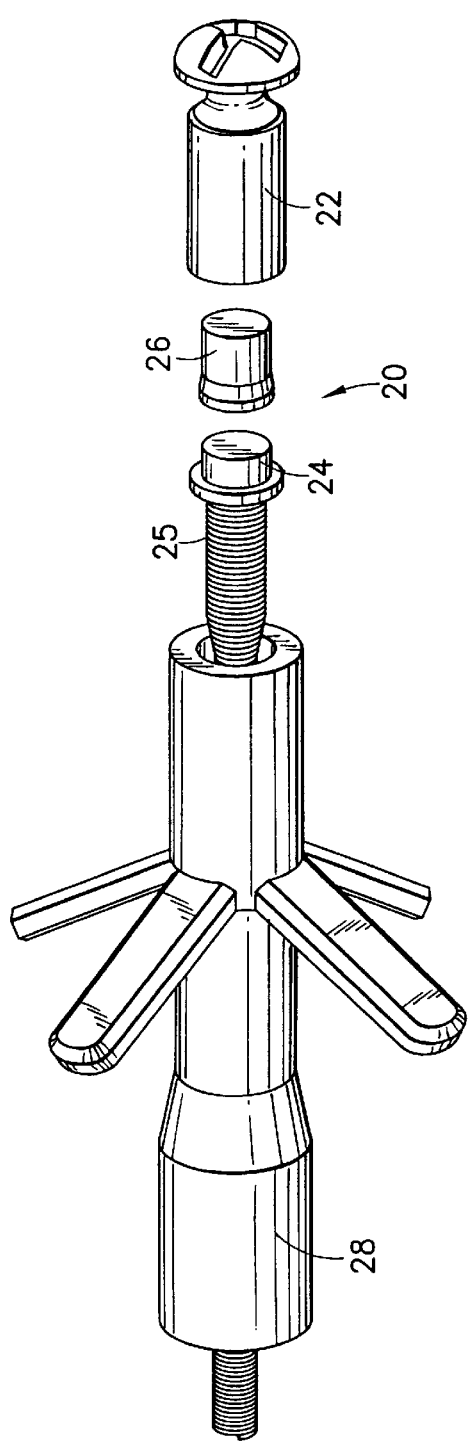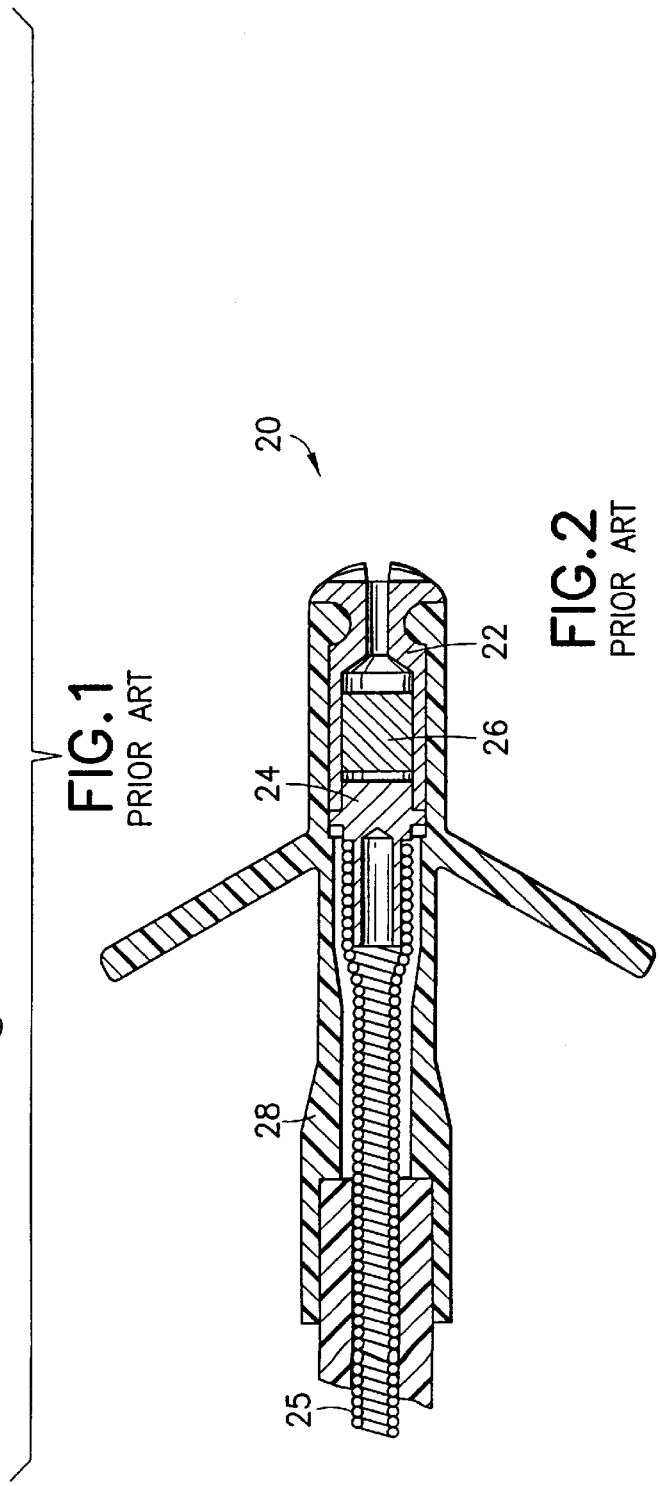
FIG. 1
PRIOR ART
FIG. 2
PRIOR ART

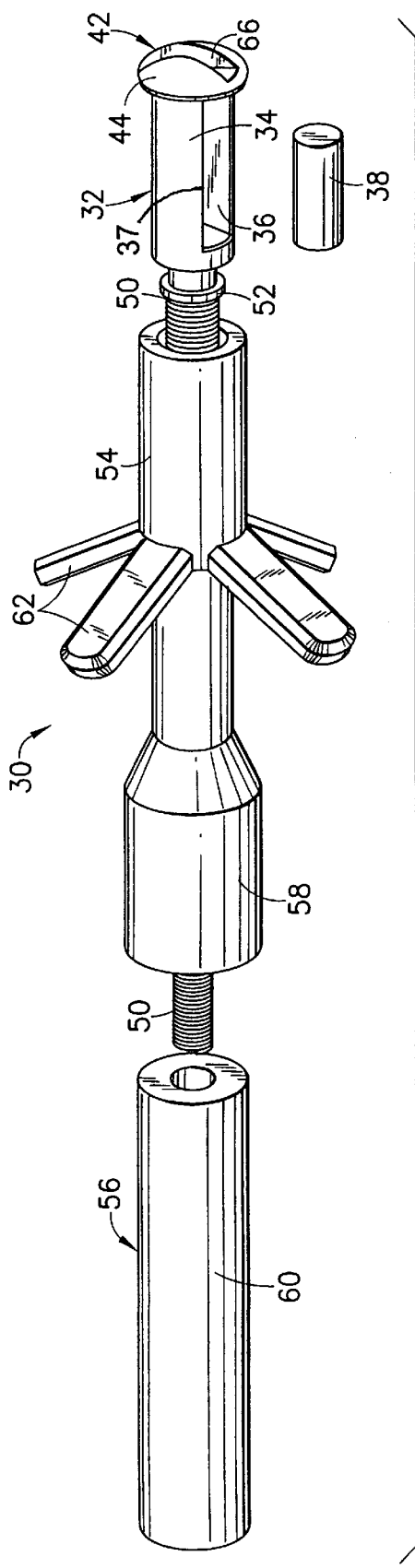
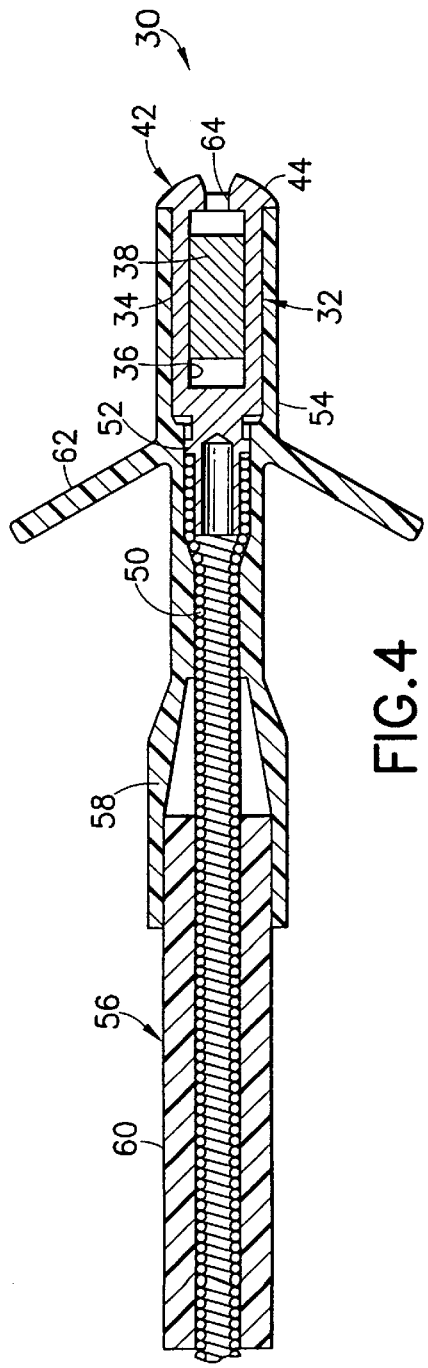
FIG.3
FIG.4

INTEGRATED STEROID ELUTING PACING TIP ELECTRODE

FIELD OF THE INVENTION

The present invention relates to body implantable leads, and more particularly, to simplified construction of steroid eluting stimulation tip electrodes.

BACKGROUND OF THE INVENTION

Typical of known passive pacing tip electrodes currently in use is a design which comprises four separate components, namely, an electrode, a weld electrode, a steroid plug, and a tine. The assembly of these components has always been a challenging one because of their very small size. First, the steroid plug is inserted into the back end of the tip electrode. Next, the weld electrode is laser welded to the back end of the tip electrode containing the steroid plug. Finally, the tine is installed onto the welded tip subassembly.

The prior art contains numerous examples of tip electrode constructions which are intended to be simplified by the present invention. In this regard, FIGS. 4 and 5 of U.S. Pat. No. 4,711,251, to Stokes, discloses an implantable lead having tines and a plug-like structure to mount a drug to be dispensed. The use of plugs, apertures, and the like within a tined lead are also typically found in U.S. Pat. Nos. 5,496,360, to Hoffmann et al.; 4,819,662, to Heil, Jr. et al.; 4,606,118, to Cannon et al.; and 4,577,642 and 4,506,680, to Stokes. Also of interest are positive fixation designs with drug elution capabilities which are disclosed in U.S. Pat. Nos. 5,003,992, to Holleman et al.; 5,002,067 and 4,953,564, to Berthelsen et al.; and 4,819,661, to Heil, Jr. et al.

It was with knowledge of the foregoing state of the technology that the present invention has been conceived and is now reduced to practice.

SUMMARY OF THE INVENTION

The present invention relates to an electrode assembly for a body implantable lead for the delivery of stimulation energy to a desired body site which comprises a longitudinally extending dispenser housing having an internal cavity with opposed longitudinally extending openings for storing a drug to be dispensed. A tip electrode integral and axially aligned with the dispenser housing has a face adapted for positioning adjacent the desired body site, a transverse channel formed into and transversely across its face, and an orifice extending between the channel and the internal cavity for elution of the drug to the desired body site. A weld sleeve integral and axially aligned with the dispenser housing distant from the tip electrode has an outer peripheral surface for engageably receiving one end of an elongated electrical conductor, and a collar spaced from the dispenser housing. The electrical conductor is welded to the collar to obtain a welded connection for electrical continuity between the tip electrode and the electrical conductor. An insulative sheath of resilient material is fittingly received on the outer peripheral surface of the dispenser housing overlying the longitudinally extending openings and the welded connection between the electrical conductor and the weld sleeve. Insulative tubing is received on the coiled conductor and includes a skirt member distant from the tip electrode and coaxial with the insulative tubing and biased radially into engagement with the outer peripheral surface of the insulative tubing. A plurality of fixation tines are integral with, and extend radially outwardly from, the insulative sheath at a plurality of circumferentially spaced locations.

A primary feature, then, of the present invention is the provision of a simplified construction for steroid eluting pacing tip electrodes.

Another feature of the present invention is the provision of such a steroid eluting pacing tip electrode comprising a longitudinally extending dispenser housing having an outer peripheral surface and an internal cavity for storing a drug to be dispensed, the internal cavity having opposed longitudinally extending openings through the peripheral surface, a tip electrode integral and axially aligned with the dispenser housing and having a face adapted for positioning at least adjacent the desired body site, and a weld sleeve integral and axially aligned with the dispenser housing distant from the tip electrode and having an outer peripheral surface for engageably receiving one end of an elongated electrical conductor.

Still another feature of the present invention is the provision of such a steroid eluting pacing tip electrode wherein the tip electrode has an orifice extending between the face thereof and the internal cavity of the longitudinally extending dispenser housing for elution of the drug to the desired body site.

Still another feature of the present invention is the provision of such a steroid eluting pacing tip electrode wherein the tip electrode has a transverse channel formed into, and extending transversely across the face of the tip electrode, the orifice enabling communication between the internal cavity and the transverse channel for elution of the drug to the desired body site.

Yet another feature of the present invention is the provision of such a steroid eluting pacing tip electrode wherein the weld sleeve includes a collar spaced from the dispenser housing; and including an elongated coiled electrical conductor coaxially received on the weld sleeve and welded to the sleeve to obtain a welded connection for electrical continuity between the tip electrode and the electrical conductor and an insulative sheath fittingly received on the outer peripheral surface of the dispenser housing overlying the longitudinally extending openings and the welded connection between the electrical conductor and the weld sleeve.

Yet a further feature of the present invention is the provision of such a steroid eluting pacing tip electrode including a plurality of tines integral with the insulative sheath, respectively, and projecting radially outwardly at a plurality of circumferentially spaced locations.

Still a further feature of the present invention is the provision of such a steroid eluting pacing tip electrode including insulative tubing received on the coiled conductor extending from a first end adjacent the dispenser housing to a second end distant therefrom and having an outer peripheral surface and wherein the insulative sheath is of resilient material and includes a skirt member distant from the tip electrode and coaxial with the insulative tubing and biased radially into engagement with the outer peripheral surface of the insulative tubing.

Still another feature of the present invention is the provision of such a steroid eluting pacing tip electrode assembly of simplified design with fewer parts resulting in lower cost and a simplified assembly process.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and together with the description, serve to explain the principles of the invention in general terms. Like numerals refer to like parts throughout the disclosure.

BRIEF DESCRIPTION OF THE DRAWINGS

FIG. 1 is an exploded view in perspective of a known tip electrode assembly;

FIG. 2 is a cross section view of the known tip electrode assembly of FIG. 1;

FIG. 3 is an exploded view in perspective of a tip electrode assembly embodying the present invention;

FIG. 4 is a cross section view of the novel tip electrode assembly of FIG. 3;

DETAILED DESCRIPTION OF THE PREFERRED EMBODIMENT

Figure 5:
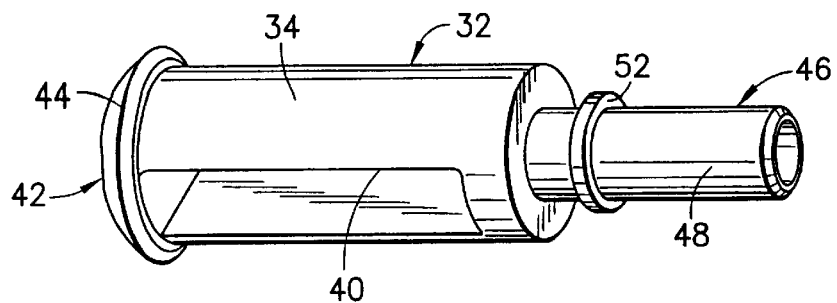
FIG. 5 is a detail perspective view of one component illustrated in FIGS. 3 and 4.

Refer now initially to FIGS. 1 and 2 which are illustrative of an existing pacing tip electrode assembly 20. FIG. 1 is an exploded perspective view of the electrode assembly 20 while FIG. 2 is a longitudinal cross sectional view of the same electrode assembly. The known pacing tip electrode assembly 20 is seen to comprise four different parts, namely, tip electrode 22, weld electrode 24, steroid plug 26, and tine sheath 28. It poses a distinct challenge to assemble these components because of their small size. To this end, first, the steroid plug 26 is inserted into the back end of the tip electrode 22. Next, the weld electrode 24 with attached conductor 25 is laser welded to the back end of the tip electrode containing the steroid plug. Finally, the tine sheath 28 is installed onto the welded tip subassembly comprising tip electrode 22, weld electrode 24, and steroid plug 26.

A newly designed pacing tip electrode assembly 30 illustrated initially in FIGS. 3 and 4 and embodying the present invention serves to simplify this known design. In this instance, the first two parts of the known electrode assembly are integrated into one single part as shown in FIGS. 3 and 4. No laser welding is required as is needed for the existing design. The steroid plug is installed into the tip electrode through the side cut on the electrode. Finally, the tine sheath is installed on the electrode assembly and creates an enclosure for the steroid plug.

Although the present invention will be described with reference to the single embodiment shown in the drawings, it should be understood that the present invention can be embodied in many alternate forms of embodiments. In addition, any suitable size, shape or type of elements or materials could be used.

Figure 6:
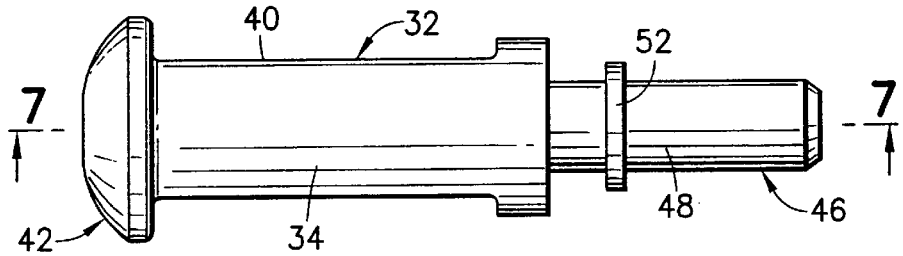
FIG. 6 is a top plan view of the component illustrated in FIG. 5.
Figure 7:
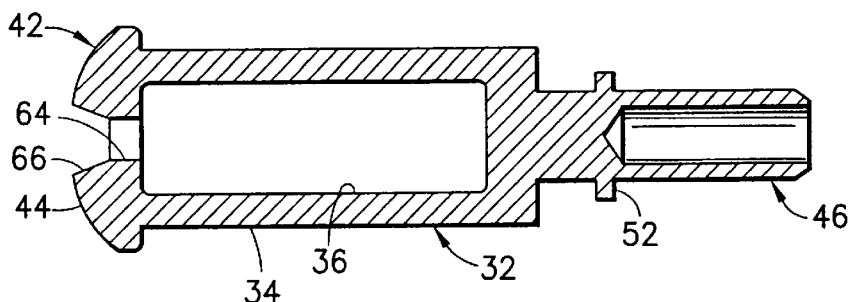
FIG. 7 is a cross section view take generally along line 7—7 in FIG. 6.
Figure 8:
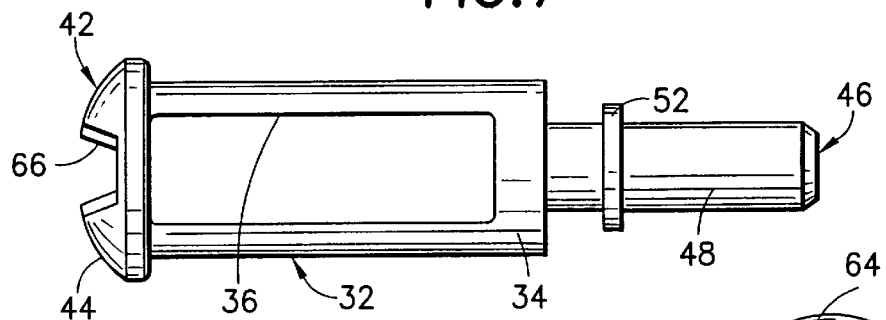
FIG. 8 is a side elevation view of the component illustrated in FIGS. 5, 6, and 7.
Figure 9:
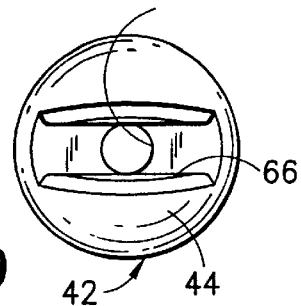
FIG. 9 is an end elevation view of the component illustrated in FIGS. 5, 6, 7, and 8.

More specifically, with continued reference to FIGS. 3 and 4, and now with reference also to FIGS. 5–9, the tip electrode assembly 30 of the invention comprises a longitudinally extending dispenser housing 32 which has an outer peripheral surface 34 and an internal cavity 36 for storing a drug to be dispensed. The drug may be in the form of a cylindrical plug herein referred to as a steroid plug 38. The steroid plug 38 has a solid but soft or pliant composition and may be a mixture of silicone rubber and a steroid mixture although it may incorporate any suitable drug intended to accomplish any desired localized purpose. The internal cavity has opposed longitudinally extending openings 37 through the peripheral surface 34 which expose the internal cavity 36 to the outside. A tip electrode 42 is integral with and axially aligned with the dispenser housing 32 and has a face 44 adapted for positioning adjacent the desired body site to be treated.

A weld sleeve 46 is also integral and axially aligned with the dispenser housing 32 distant from the tip electrode 42 and has an outer peripheral surface 48 for engageably receiving one end of an elongated electrical conductor 50, typically of a coiled configuration. In a preferred design, the weld sleeve 46 includes a collar 52 spaced from the dispenser housing 32. The collar 52 is integral with or fixed to the weld sleeve. The elongated coiled electrical conductor 50 is coaxially received on the weld sleeve and, typically by means of laser welding is securely attached to the sleeve to thereby obtain a welded connection for electrical continuity between the tip electrode 42 and the electrical conductor.

An insulative sheath 54 is fittingly received on the outer peripheral surface 34 of the dispenser housing 32 overlying the longitudinally extending openings (see FIG. 4) and the welded connection between the electrical conductor and the weld sleeve. Also, insulative tubing 56 is received on the coiled conductor 50 and extends from one end somewhat adjacent the dispenser housing 32 to another distant end which may be adjacent the stimulating device (not shown). The insulative sheath 54 is preferably of resilient biocompatible material such as silicone rubber and includes a skirt member 58 distant from the tip electrode 42 and coaxial with the insulative tubing 56 and biased radially into engagement with an outer peripheral surface 60 of the insulative tubing. A plurality of tines 62 are formed as part of the insulative sheath, integral therewith and project radially outwardly therefrom, respectively, at a plurality of circumferentially spaced locations. The tines 62 are employed in a known manner to secure the tip electrode assembly 30 to the selected myocardial location.

The tip electrode 42 is formed with an orifice 64 extending between the face 44 and the internal cavity 36 of the dispenser housing 32 for elution of the drug to the desired body site. Prior to use, the steroid plug may be soaked in a solution of the desired drug until fully saturated. Thereupon, when the tip electrode assembly is implanted, body fluids enter the internal cavity 36 through the orifice 64, intermingle with the drug, and carry the drug back out through the orifice for deposit onto the face 44 of the tip electrode. To improve the efficiency of the elution path and to avoid the possible occurrence of an air lock preventing elution through the orifice 64, it is desirable that the length of the orifice be minimized. Accordingly, the tip electrode 42 is preferably formed with a transverse channel 66 which extends across its face 44. In this instance, the orifice 64 enables communication between the internal cavity 36 and first the transverse channel 66, then to the face 44 for elution of the drug to the desired body site. With this construction, the length of the orifice 64 is minimized without adversely effecting elution of the drug to the face 44.

While preferred embodiments of the invention have been disclosed in detail, it should be understood by those skilled in the art that various other modifications may be made to the illustrated embodiments without departing from the scope of the invention as described in the specification and defined in the appended claims.

What is claimed is:

1. An electrode assembly for a body implantable lead for the delivery of stimulation energy to a desired body site comprising:

a longitudinally extending dispenser housing having an outer peripheral surface and an internal cavity for storing a drug to be dispensed, the internal cavity having at least one longitudinally extending opening through the peripheral surface suitable for receiving an elongated plug containing the drug to be dispensed;

tip electrode integral and axially aligned with the dispenser housing and having a face adapted for positioning at least adjacent the desired body site; and a weld sleeve integral and axially aligned with the dispenser housing distant from the tip electrode and having an outer peripheral surface for engageably receiving one end of an elongated electrical conductor.

2. The electrode assembly, as set forth in claim 1, wherein the tip electrode has an orifice extending between the face thereof and the internal cavity of the longitudinally extending dispenser housing for elution of the drug to the desired body site.

3. The electrode assembly, as set forth in claim 2, wherein the tip electrode has a transverse channel formed into, and extending transversely across the face of the tip electrode, the orifice enabling communication between the internal cavity and the transverse channel for elution of the drug to the desired body site.

4. The electrode assembly, as set forth in claim 2, wherein the tip electrode has a circular outer peripheral surface and a diametrically extending channel formed into and across the face thereof, the orifice enabling communication between the internal cavity and the transverse channel for elution of the drug to the desired body site.

5. The electrode assembly, as set forth in claim 1, including:

an elongated coiled electrical conductor coaxially received on the weld sleeve and welded thereto to obtain a welded connection for electrical continuity between the tip electrode and the electrical conductor; and insulative sheath fittingly received on the outer peripheral surface of the dispenser housing overlying the longitudinally extending openings and the welded connection between the electrical conductor and the weld sleeve.

6. The electrode assembly, as set forth in claim 1, wherein the weld sleeve includes a collar spaced from the dispenser housing; and including:

an elongated coiled electrical conductor coaxially received on the weld sleeve and welded to the sleeve to obtain a welded connection for electrical continuity between the tip electrode and the electrical conductor; and an insulative sheath fittingly received on the outer peripheral surface of the dispenser housing overlying the longitudinally extending openings and the welded connection between the electrical conductor and the weld sleeve.

7. The electrode assembly, as set forth in claim 5, including:

a plurality of tines integral with the insulative sheath and projecting radially outwardly therefrom, respectively, at a plurality of circumferentially spaced locations.

8. The electrode assembly, as set forth in claim 6, including:

a plurality of tines integral with the insulative sheath and projecting radially outwardly therefrom, respectively, at a plurality of circumferentially spaced locations.

9. The electrode assembly, as set forth in claim 6, including:

insulative tubing received on the coiled conductor extending from a first end adjacent the dispenser housing to a second end distant therefrom and having an outer peripheral surface; and wherein the insulative sheath is of resilient material and includes a skirt member distant from the tip electrode and coaxial with the insulative tubing and biased radially into engagement with the outer peripheral surface of the insulative tubing.

10. The electrode assembly, as set forth in claim 1, wherein the at least one longitudinally extending opening is comprised of opposed longitudinally extending openings.

11. The electrode assembly, as set forth in claim 10, wherein the elongate plug is cylindrically shaped.

12. The electrode assembly, as set forth in claim 1, wherein the elongate plug is cylindrically shaped.

* * * * *